United States Patent
Kasper et al.

(10) Patent No.: US 10,668,207 B2
(45) Date of Patent: Jun. 2, 2020

(54) SYSTEM AND METHOD FOR REMOVING FAT FROM SALVAGED BLOOD

(71) Applicant: Haemonetics Corporation, Braintree, MA (US)

(72) Inventors: Seth Kasper, Cambridge, MA (US); Jordan Smelker, Somerville, MA (US); Samuel Vaughan, Somerville, MA (US)

(73) Assignee: Haemonetics Corporation, Boston, MA (US)

(*) Notice: Subject to any disclaimer, the term of this patent is extended or adjusted under 35 U.S.C. 154(b) by 318 days.

(21) Appl. No.: 15/577,005

(22) PCT Filed: Jul. 13, 2016

(86) PCT No.: PCT/US2016/042038
§ 371 (c)(1),
(2) Date: Nov. 27, 2017

(87) PCT Pub. No.: WO2017/011527
PCT Pub. Date: Jan. 19, 2017

(65) Prior Publication Data
US 2018/0154065 A1    Jun. 7, 2018

Related U.S. Application Data

(60) Provisional application No. 62/191,823, filed on Jul. 13, 2015.

(51) Int. Cl.
*A61M 1/38* (2006.01)
*A61M 1/36* (2006.01)
*A61M 1/02* (2006.01)

(52) U.S. Cl.
CPC ........ *A61M 1/3692* (2014.02); *A61M 1/0209* (2013.01); *A61M 1/0281* (2013.01);
(Continued)

(58) Field of Classification Search
CPC .............. A61M 1/0209; A61M 1/0281; A61M 1/3692; A61M 1/3693; A61M 1/38;
(Continued)

(56) References Cited

U.S. PATENT DOCUMENTS 4,151,844 A    5/1979   Cullis et al.
4,482,342 A    11/1984  Lueptow et al.
(Continued)

FOREIGN PATENT DOCUMENTS

GB         2250699 A       6/1992
WO      1989/01792 A1     3/1989

OTHER PUBLICATIONS

International Search Report and Written Opinion for Application No. PCT/US2016/042038, dated Oct. 5, 2016, 13 pages.

*Primary Examiner* — Timothy C Cleveland
(74) *Attorney, Agent, or Firm* — McCarter & English, LLP; Jonathan C. Lovely (57) ABSTRACT

A method for removing fat from salvaged blood includes transferring salvaged blood from a reservoir to a blood component separation device, and separating the blood into a plurality of blood components. The method may then transfer a volume of unwashed blood components from the blood component separation device back toward the reservoir, and re-centrifuge the blood components remaining within the blood component separation device. After re-centrifuging, the method transfers additional salvaged blood from the reservoir to the blood component separation device to refill the blood component separation device. The method may then wash the components within the bowl by introducing wash solution into the blood component separation device. The wash solution displaces a volume of fat from the blood component separation device and into a waste container. The method may then empty the washed blood
(Continued)

components within the blood component separation device to a product container.

52 Claims, 10 Drawing Sheets

(52) U.S. Cl.
CPC ............ *A61M 1/3693* (2013.01); *A61M 1/38* (2013.01); *A61M 2202/0021* (2013.01); *A61M 2202/0085* (2013.01); *A61M 2202/0092* (2013.01); *A61M 2202/0413* (2013.01); *A61M 2202/08* (2013.01)

(58) Field of Classification Search
CPC .. A61M 2202/0021; A61M 2202/0085; A61M 2202/0092; A61M 2202/0413; A61M 2202/08
See application file for complete search history.

(56) References Cited

U.S. PATENT DOCUMENTS

| | | |
|---|---|---|
| 4,668,214 A | 5/1987 | Reeder |
| 4,806,252 A | 2/1989 | Brown et al. |
| 4,828,716 A | 5/1989 | McEwen et al. |
| 4,834,890 A | 5/1989 | Brown et al. |
| 4,943,273 A | 7/1990 | Pages |
| 5,053,121 A | 10/1991 | Schoendorfer et al. |
| 5,076,911 A | 12/1991 | Brown et al. |
| 5,308,506 A | 5/1994 | McEwen et al. |
| 5,344,570 A | 9/1994 | McLachlan et al. |
| 5,385,539 A | 1/1995 | Maynard |
| 5,478,479 A | 12/1995 | Herrig |
| 2010/0069215 A1 | 3/2010 | Lee et al. |
| 2013/0045852 A1 | 2/2013 | Chapman et al. |
| 2015/0314060 A1 | 11/2015 | Maculan et al. |

Fig. 8

SYSTEM AND METHOD FOR REMOVING FAT FROM SALVAGED BLOOD

PRIORITY

This patent application claims priority from U.S. Provisional Patent Application No. 62/191,823, filed Jul. 13, 2015, entitled, "System and Method for Removing Fat from Salvaged Blood,", and naming Seth Kasper, Jordan Smelker and Samuel Vaughan as inventors, the disclosure of which is incorporated herein, in its entirety, by reference.

TECHNICAL FIELD

The present invention relates to the collection of shed blood, and more particularly to washing fat from shed blood.

BACKGROUND ART

In many applications it is desirable to drain and collect blood and other fluids from wounds and surgical sites (e.g., intra-operatively and/or post-operatively). Not only does the removal of fluids aid in healing and reduce the threat of infection, when blood is collected, it provides the hospital the opportunity to return the collected blood back to the patient. This, in turn, reduces the need to transfuse blood that is not the patient's own blood (e.g., allogeneic blood).

Prior-art systems for salvaging blood from surgical sites and wound drains often employ disposable units that include a reservoir for collecting the blood. The collected blood may then be re-infused into the patient. However, in many instances, the collected blood is not washed prior to being re-infused into the patient. Rather, the prior art systems merely pass the collected blood through a micro-aggregate blood filter to remove aggregates from the blood.

SUMMARY OF THE EMBODIMENTS

In accordance with one embodiment of the invention, a method for removing fat from salvaged whole blood includes transferring salvaged/shed blood from a reservoir to a blood component separation device (e.g., to fill the blood component separation device). The method may then separate the salvaged/shed blood into a plurality of blood components, transfer a volume of the unwashed blood components from the blood component separation device back to/toward the reservoir, and re-centrifuge the blood components remaining within the blood component separation device. After re-centrifuging, the method may (1) transfer additional salvaged/shed blood from the reservoir to the blood component separation device to refill the blood component separation device, and (2) wash the components within the separation device. For example, the method may introduce wash solution into the blood component separation device, which, in turn, displaces a volume of fat from the blood component separation device into a waste container. After washing, the method may empty the washed blood components within the blood component separation device to a product container. At least a portion of the volume of unwashed blood components transferred back to the reservoir may remain within a reservoir line fluidly connecting the reservoir and the blood component separation device. The additional salvaged blood may include the volume of unwashed blood components transferred back toward the reservoir.

In some embodiments, the method may also, prior to emptying the washed blood components to the product container, transfer a volume of washed blood components from the blood component separation device to the product container. The method may then re-centrifuge the washed blood components remaining within the blood component separation device, and return the volume of washed blood components from the product container to the blood component separation device (e.g., to refill the blood component separation device). After refilling, the method may introduce additional wash solution into the blood component separation device. The additional wash solution may displace a second volume of fat from the blood component separation device and into a waste container.

The blood component separation device may be a 70 mL centrifuge bowl, and the volume of unwashed blood component transferred to the reservoir may be between 20 and 30 mL. Additionally or alternatively, the volume of additional salvaged/shed blood transferred to the separation device may be equivalent to the volume of unwashed blood component transferred to the reservoir. In some embodiments, the volume of washed blood components transferred to the product container may be between 20 and 30 mL, and introducing additional wash solution into the blood component separation device may include introducing 50 ml of wash solution.

In alternative embodiments, the blood component separation device may be a 125 mL centrifuge bowl. In such embodiments, the volume of unwashed blood component transferred to the reservoir may be between 20 and 30 mL. Additionally or alternatively, the volume of additional salvaged/shed blood transferred to the separation device may be equivalent to the volume of unwashed blood component transferred to the reservoir. The volume of washed blood components transferred to the product container may be between 80 and 100 mL, and introducing additional wash solution into the blood component separation device may include introducing 100 ml of wash solution.

In further embodiments, the blood component separation device may be a 225 mL centrifuge bowl, and the volume of unwashed blood component transferred to the reservoir may be between 20 and 30 mL. The volume of additional salvaged/shed blood transferred to the separation device may be equivalent to the volume of unwashed blood component transferred to the reservoir. The volume of washed blood components transferred to the product container may be between 160 and 180 mL, and introducing additional wash solution into the blood component separation device may include introducing 100 ml of wash solution.

The method may also include (1) monitoring the separation of salvaged/shed blood within the blood component separation device to detect when the blood component separation device is full, and (2) stopping the blood component separation device when the blood component separation device is full and prior to transferring the volume of unwashed blood components from the separation device to the reservoir. The volume of unwashed blood components transferred to the reservoir may include red blood cells. Additionally or alternatively, re-centrifuging the blood components within the separation device may cause fat within the blood component separation device to pass through a red blood cell product within the blood component separation device and toward an outlet of the blood component separation device.

In accordance with further embodiments, a method for removing fat from salvaged salvaged/shed blood includes transferring salvaged/shed blood from a reservoir to a blood component separation device (e.g., filling the blood component separation device), and separating the salvaged/shed blood into a plurality of blood components. The method may then wash the blood components by introducing wash solution into the blood component separation device. The wash solution may displace a volume of unwanted components from the blood component separation device into a waste container. The method may then transfer a volume of washed blood components from the blood component separation device to a product container, re-centrifuge the washed blood components remaining within the blood component separation device, and return the volume of washed blood components from the product container to the blood component separation device (e.g., to refill the blood component separation device). The method may also introduce additional wash solution into the blood component separation device to displace a volume of fat from the blood component separation device into a waste container. The method may then empty the washed blood components within the blood component separation device to a product container.

In some embodiments, the method may stop the blood component separation device prior transferring the volume of washed blood components to the product container. The blood component separation device may be a 70 mL centrifuge bowl, a 125 mL centrifuge bowl, or a 225 mL centrifuge bowl. The volume of washed blood components transferred to the product container may be between 20 and 30 mL, and introducing the additional wash solution into the blood component separation device may include introducing 50 mL of wash solution for 70 mL bowl, and 100 ml of wash solution for 125 and 225 mL bowls. Alternatively, the volume of washed blood components transferred to the product container may be between 20 and 30 mL, 80 and 100 mL, or between 160 and 180 mL.

In accordance with still further embodiments, a system for washing fat from salvaged blood includes a reservoir configured to collect salvaged blood from a patient, and a rotatable centrifuge bowl fluidly connected to the reservoir and configured to separate the salvaged blood into a plurality of blood components. The system may also have (1) a product container fluidly connected to the rotatable centrifuge bowl and configured to collect a washed blood component, (2) a waste container fluidly connected to an outlet of the rotatable centrifuge bowl and configured to collect a waste product from the centrifuge bowl, and (3) a pump configured to control the flow of fluid through the system. The system may further include a controller configured to control the operation of the pump and centrifuge bowl. For example, the controller may control the pump/system such that (1) the pump transfers a first volume of unwashed blood components from the centrifuge bowl back to the reservoir, (2) the centrifuge bowl re-centrifuges the blood components remaining within the centrifuge bowl, (3) the pump refills the centrifuge bowl with salvaged/shed blood from the reservoir, and (4) the pump introduces wash solution into the centrifuge bowl. The wash solution may displace a volume of fat from the centrifuge bowl into the waste container.

In some embodiments, the controller may be further configured to empty the washed blood components within the centrifuge bowl to the product container. Additionally or alternatively, the controller may be configured to control the pump and centrifuge bowl to (1) transfer a volume of washed blood components from the blood component separation device to the product container, (2) re-centrifuge the washed blood components remaining within the blood component separation device, (3) return the volume of washed blood components from the product container to the blood component separation device (e.g., to refill the blood component separation device), and/or (4) control the pump to introduce additional wash solution into the centrifuge bowl. The additional wash solution may displace a second volume of fat from the centrifuge bowl into the waste container.

The centrifuge bowl may be a 70 mL centrifuge bowl, a 125 mL centrifuge bowl, or a 225 mL centrifuge bowl. The system may also include an optical sensor configured to monitor the separation of salvaged/shed blood within the centrifuge bowl and detect when the centrifuge bowl is full. The first volume of unwashed blood components may include red blood cells.

In accordance with additional embodiments, a method for removing fat from salvaged blood includes transferring salvaged blood from a reservoir to a blood component separation device (e.g., to fill the blood component separation device). The method may then separate the salvaged blood into a plurality of blood components, transfer a volume of unwashed blood components from the blood component separation device back to a reservoir line fluidly connecting the reservoir and the blood component separation device, and re-centrifuge the blood components remaining within the blood component separation device. After re-centrifuging, the method may (1) return the volume of unwashed blood components from the reservoir line to the blood component separation device to refill the blood component separation device, and (2) introduce wash solution into the blood component separation device. The wash solution may displace a volume of fat from the blood component separation device into a waste container. The method may then empty the washed blood components within the blood component separation device to a product container.

In some embodiments, the method may also transfer, prior to emptying the washed blood components to the product container, a volume of washed blood components from the blood component separation device to the product container. The method may then re-centrifuge the washed blood components remaining within the blood component separation device, and return the volume of washed blood components from the product container to the blood component separation device to refill the blood component separation device. After refilling, the method may introduce additional wash solution into the blood component separation device to displace a second volume of fat from the blood component separation device into a waste container.

The blood component separation device may be a 70 mL centrifuge bowl, and the volume of unwashed blood component transferred to the reservoir line may be between 20 and 30 mL. Additionally or alternatively, the volume of washed blood components transferred to the product container may be between 20 and 30 mL, and/or introducing additional wash solution into the blood component separation device may include introducing 50 ml of wash solution.

In other embodiments, the blood component separation device may be a 125 mL centrifuge bowl, and the volume of unwashed blood component transferred to the reservoir line may be between 20 and 30 mL. The volume of washed blood components transferred to the product container may be between 80 and 100 mL, and introducing additional wash solution into the blood component separation device may include introducing 100 ml of wash solution. Alternatively, the blood component separation device may be a 225 mL centrifuge bowl, and the volume of unwashed blood component transferred to the reservoir line may be between 20 and 30 mL. In such embodiments, the volume of washed blood components transferred to the product container may be between 160 and 180 mL, and introducing additional wash solution into the blood component separation device may include introducing 100 ml of wash solution.

The method may also include (1) monitoring the separation of salvaged blood within the blood component separation device to detect when the blood component separation device is full, and (2) stopping the blood component separation device when the blood component separation device is full and prior to transferring the volume of unwashed blood components to the reservoir line. The volume of unwashed blood components transferred to the reservoir line may include red blood cells and/or red blood cells suspended in plasma. Re-centrifuging the blood components remaining within the blood component separation device may cause fat within the blood component separation device to pass through a red blood cell product within the blood component separation device and toward an outlet of the blood component separation device. The method may stop the blood component separation device prior to transferring the volume of unwashed blood components to the reservoir line.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
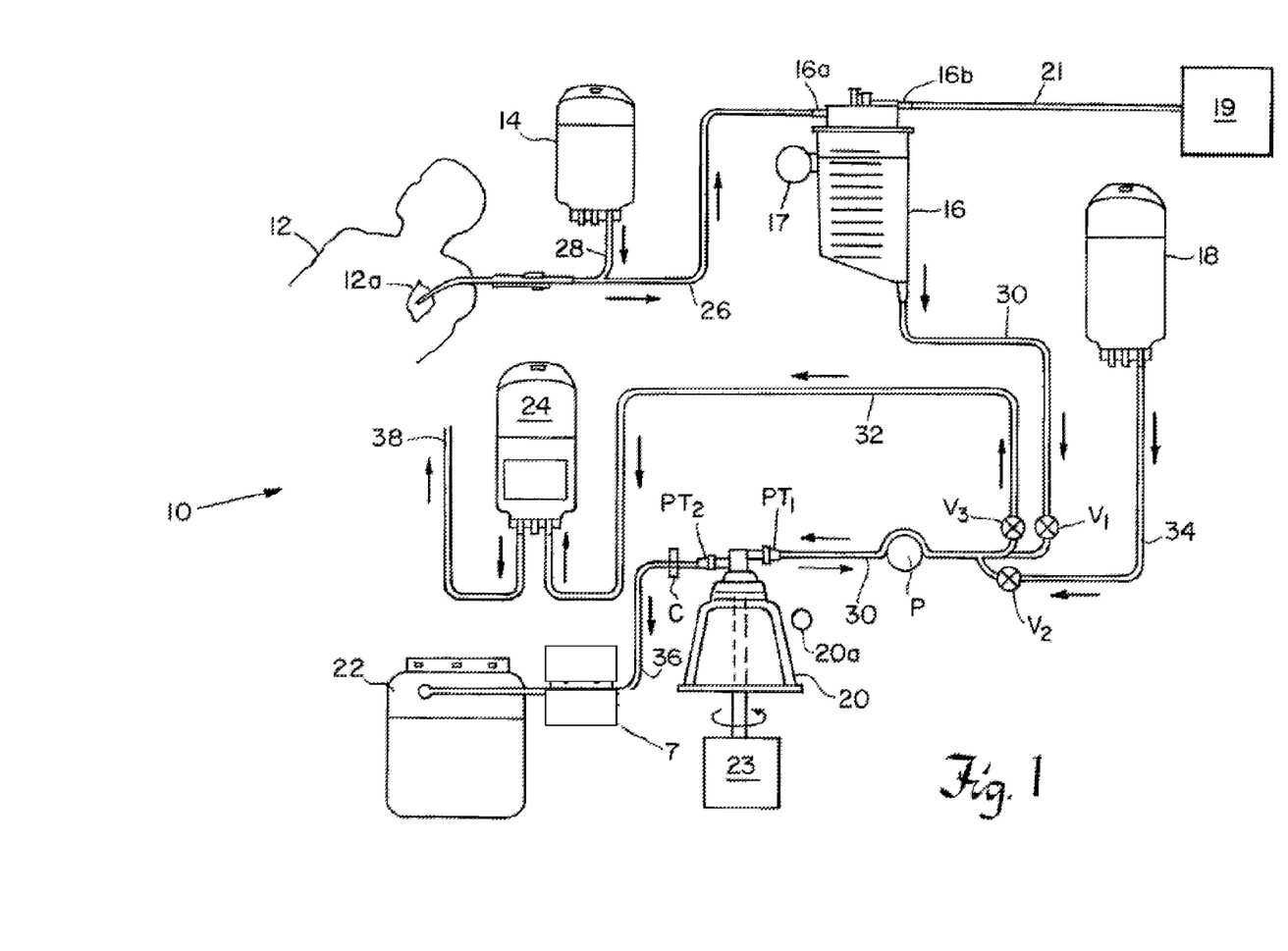
FIG. 1 schematically shows a cell salvage and washing system in accordance with embodiments of the present invention.

FIG. 1 shows a cell washing apparatus 10 in accordance with some embodiments of the present invention. The washing apparatus 10 includes a suction line 26 for suctioning blood lost from a wound site 12a (or surgical site) of a patient 12. The suction line 26 is in fluid communication with a salvage reservoir 16 via a port 16a (e.g., an inlet port). A bag 14, containing anticoagulant, is in fluid communication with the suction line 26 via a feed line 28. A vacuum source 19 is coupled to a port 16b (e.g., a vacuum port) of the reservoir 16 via a vacuum line 21. The vacuum source 19 provides a vacuum within the suction line 26 so that the suction line 26 can suction blood from the wound/surgical site 12a into the reservoir 16. As discussed in greater detail below, a reservoir level sensor 17 senses the level of fluid within the reservoir 16.

Figure 2:
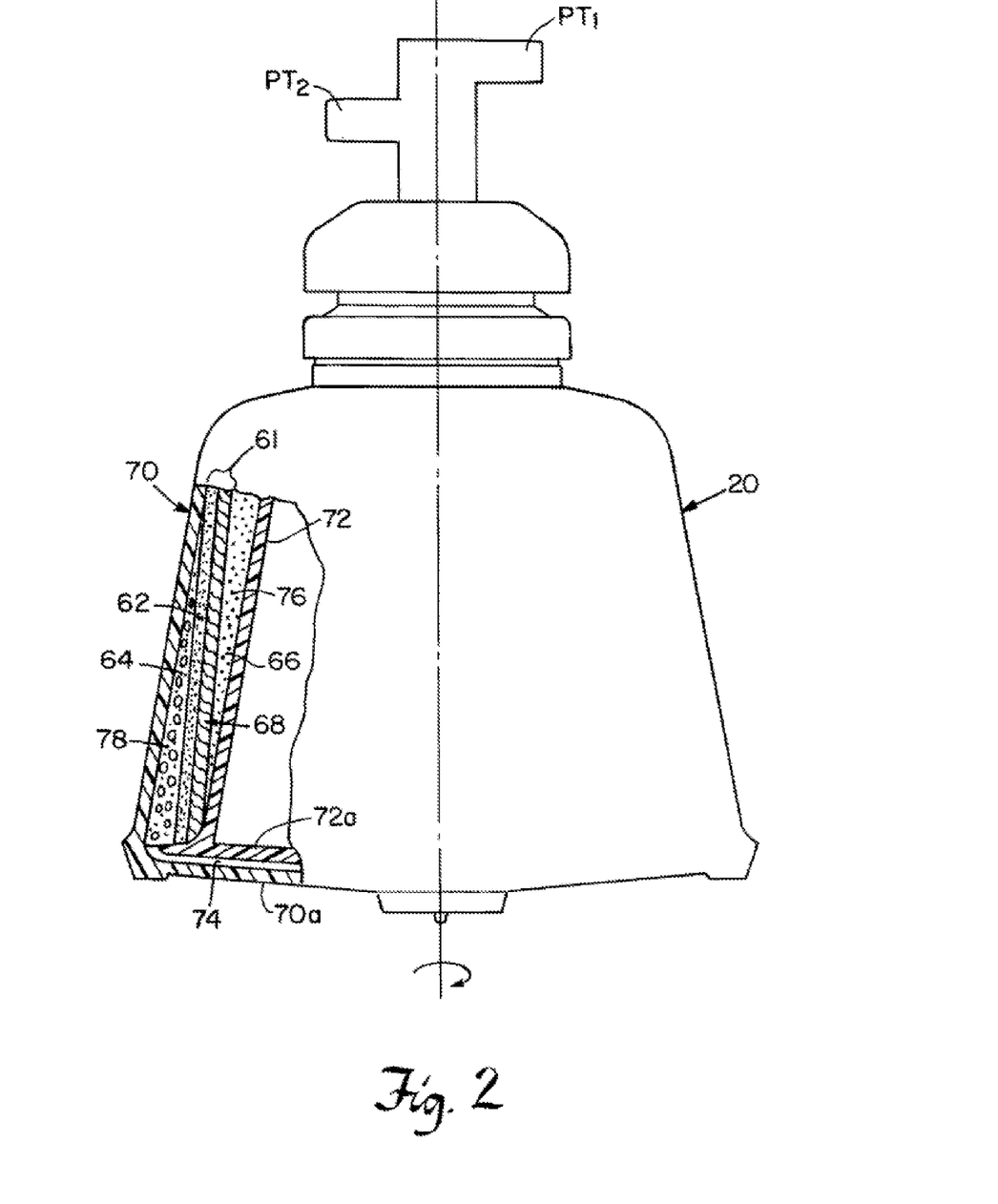
FIG. 2 is a side view of a centrifuge bowl with a portion of the wall removed to show the separation of blood components within the bowl, in accordance with embodiments of the present invention.

The reservoir 16 is in fluid communication with a centrifuge bowl 20 via line 30, valve $V_1$, and the inlet port $PT_1$. The centrifuge 20 separates and washes salvaged blood received from the reservoir 16, and is rotated by a motor 23. An optical sensor 20a directed towards/aimed at the bowl 20 senses the level of hematocrit within the centrifuge bowl 20 by directing a beam of light into the centrifuge bowl 20 which is reflected back to the sensor 20a by a core 72 within the bowl 20 (FIG. 2). If the beam of light is not reflected back to the sensor 20a, the centrifuge bowl 20 is considered full of red blood cells (the bowl hematocrit is approximately 45%-55%).

As shown in FIG. 1, a waste container 22 for collecting waste washed from the salvaged blood is fluidly coupled to the centrifuge bowl 20 via the outlet port $PT_2$, and an effluent line 36. The effluent line 36 passes through an optical line sensor 7 which senses the turbidity of the fluid flowing through the effluent line 36. The optical line sensor 7 may also control the speed of the pump P, the number of wash stages and the volume of wash solution employed for washing blood components. To facilitate the wash process, the system 10 may have a bag 18 containing a wash solution. The wash fluid container 18 may be fluidly coupled to the centrifuge bowl 20 via a wash line 34, the valve $V_2$, the line 30, and the inlet port $PT_1$.

It should be noted that in some instances, the line sensor 7 may have difficulty distinguishing fat from red blood cells (e.g., the fat removed during the fat removal/wash procedure can look like red blood cells to the sensor 7). Therefore, in some embodiments, the calibration and sensitivity of the line sensor 7 may be adjusted (e.g., the sensitivity may be decreased) so that the sensor 7 may more easily distinguish fat cells from red blood cells.

To collect the final/washed blood components (e.g., red blood cells), the system 10 also includes a collection bag 24 that, in turn, is fluidly connected to the centrifuge bowl 20 via the inlet port $PT_1$, line 30, valve $V_3$ and line 32. In some embodiments, the system 10 has a line 38 connected to an outlet of the collection bag 24. This line 38 allows fluid collected in the collection bag 24 to be transferred into a secondary reinfusion bag (not shown) in which air is removed for pressurized reinfusion into the patient 12 via a phlebotomy needle. Alternatively, the fluid collected in the collection bag 24 may be gravity fed into the patient 12 via a phlebotomy needle and line 38. Valves $V_1$, $V_2$ and $V_3$ are remotely operated to control the directional flow of fluids pumped by the pump P within the apparatus 10. The pump P may be a peristaltic pump for pumping fluids into and out of centrifuge bowl 20. Optionally, a clamp C can be included for clamping effluent line 36.

Generally, during operation, blood from the wound 12a (or surgical site) is suctioned from the patient 12 via a suction line 26. The suctioned blood is anticoagulated with anticoagulant dripping from the anticoagulant bag 14 via the feed line 28 and stored in reservoir 16. As noted above, the reservoir 16 may include a level sensor 17 that senses the level of salvaged blood within reservoir 16. Once a predetermined amount of salvaged blood is stored/has been collected within the reservoir 16, the level sensor 17 (or a controller) activates the pump P which begins what is to be referred to as the fill mode (FIG. 3) by pumping salvaged blood into the centrifuge bowl 20 from the reservoir 16 via line 30, valve $V_1$ and inlet port $PT_1$, with valve $V_1$ open and valves $V_2$ and $V_3$ closed. The rate of the pump P is controlled by the optical line sensor 7 and/or the controller.

The blood enters the separation chamber 76 of the centrifuge bowl 20 (FIG. 2) at the bottom of centrifuge bowl 20 via a feed/inlet tube 80 (FIGS. 6A-6I) and a radial passageway 74. As shown in FIG. 2, the separation chamber 76 is defined by the outer wall 70 and the core 72 of the centrifuge bowl 20. The radial passageway 74 is defined by the bottom 72a of the core 72 and the bottom wall 70a of the centrifuge bowl 20. As the centrifuge bowl 20 is filled with blood, the centrifuge bowl 20 is rotated by the motor 23, separating the blood within separation chamber 76 into different fractions in accordance with the component densities. The centrifuge bowl 20 is preferably rotated at speeds ranging from about 4,800 to 5,650 revolutions per minute. When in the bowl 20, centrifugal forces separate the blood into higher density components (mainly red blood cells (RBCs) 64), intermediate density components (mainly white blood cells 62 and platelets 68), and lower density components (mainly plasma 66). The RBCs 64 are forced to the outer wall 70 of the centrifuge bowl 20 while the plasma 66 remains nearer to the core 72 of the centrifuge bowl 20. A "buffy coat" 61 is formed between the plasma 66 and the RBCs 64. The "buffy coat" 61 is made up of an inner layer of platelets 68 and an outer layer of white blood cells (WBCs) 62.

As the separation chamber 76 is filled with blood, the RBC layer 64 moves in radially, resulting in its boundary rising upwards. The optical sensor 20a is positioned relative to the centrifuge bowl 20 such that when the separation chamber 76 is filled (e.g., to approximately 50% hematocrit), the upwardly rising RBC layer scatters the beam of light generated by the optical sensor 20a. As a result, the optical sensor 20a does not receive a reflected beam of light from the core 72 and the optical sensor 20a determines that the centrifuge bowl 20 is full. Once the optical sensor 20a determines that the separation chamber 76 is full (e.g., to approximately 50% hematocrit), the pump P stops pumping and the filling of the centrifuge bowl 20 is terminated.

In some salvage applications (e.g., cardiac, orthopedic, etc.), the blood/fluid salvaged from the patient 12 may include fat. In such applications, as the blood is centrifuged and separated into the individual blood components, the fat, which is unable to pass through the layer of red blood cells, will become trapped at the base of the bowl 20 and behind the layer of red blood cells. Furthermore, because the fat is trapped behind the red blood cells, typical washing procedures are unable to remove the fat. To that end, various embodiments can perform a "fat wash" to remove the fat from the blood and the centrifuge bowl 20.

Figure 5:
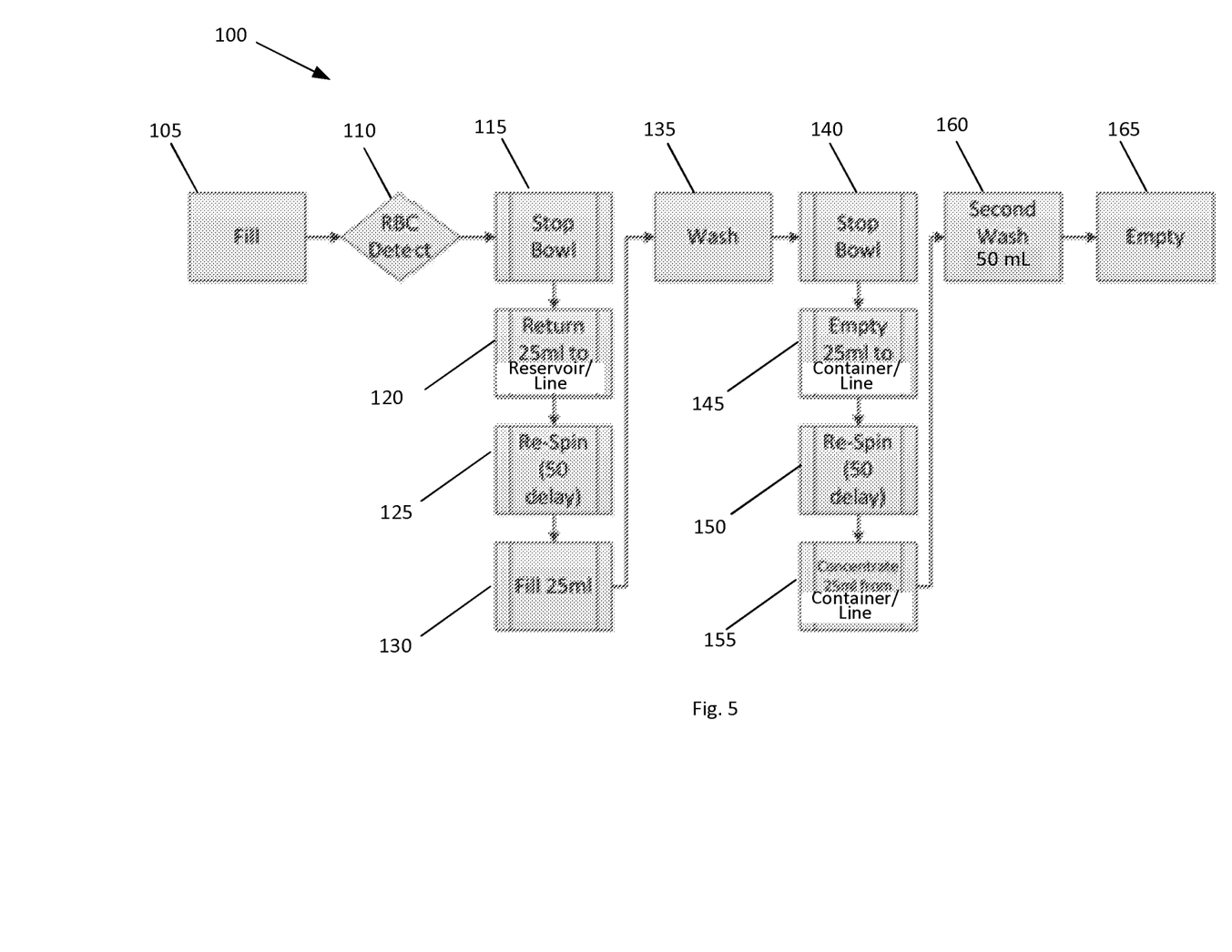
FIG. 5 is a flowchart depicting a method of washing fat from shed blood, in accordance with some embodiments of the present invention.
Figure 6A:
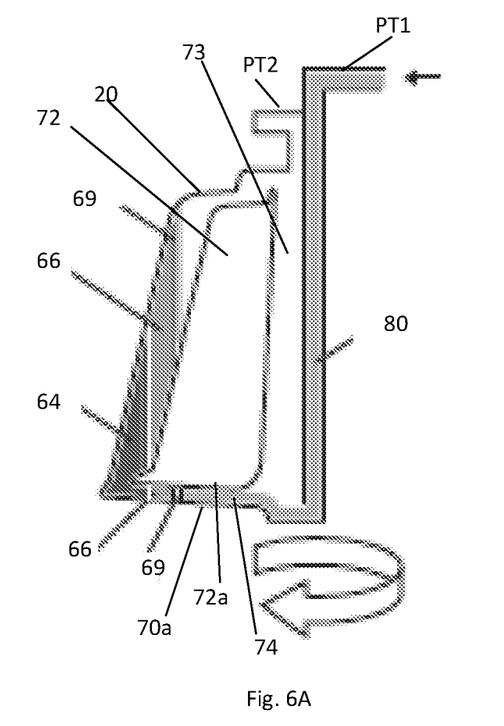
FIGS. 6A-6I schematically show a portion of the separation device and blood components within the separation device at various stages of the method shown in FIG. 5, in accordance with some embodiments of the present invention.
Figure 6B:
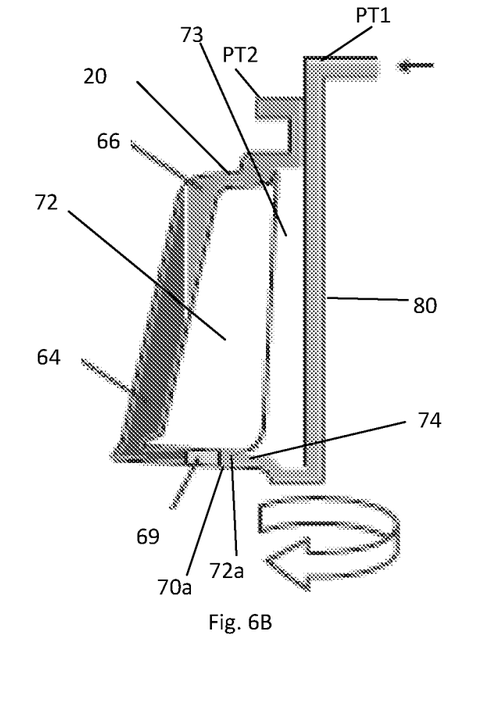

For example, FIG. 5 is a flowchart depicting a method 100 for washing fat from the collected shed blood in accordance with various embodiments of the present invention. FIGS. 6A-6I schematically show the bowl 20 (e.g., a 125 mL centrifuge bowl) and its contents at the various stages of the method. First, once the predetermined amount of salvaged blood is stored within reservoir 16 (as detected by the level sensor 17), a controller will activate the pump P and begin to fill the bowl 20 by pumping salvaged blood into the bowl 20 (Step 105). As mentioned above, as the blood enters the bowl 20, the blood will begin to separate into its individual components (FIG. 6A). During bowl filling, the controller and the optical sensor 20a will monitor the bowl 12 and the contents until the sensor 20a detects the presence of red blood cells (Step 110), indicating that the bowl 20 is full (FIG. 6B).

Figure 3:
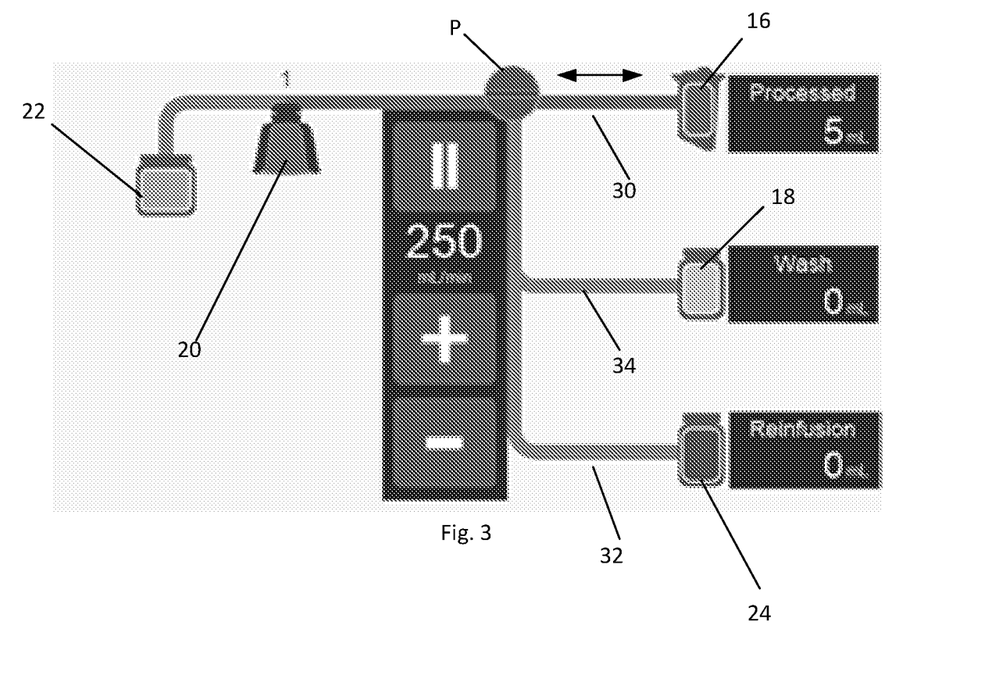
FIG. 3 schematically shows the transfer of salvaged/shed blood from a reservoir to a separation device of the system shown in FIG. 1, in accordance with embodiments of the present invention.
Figure 6C:
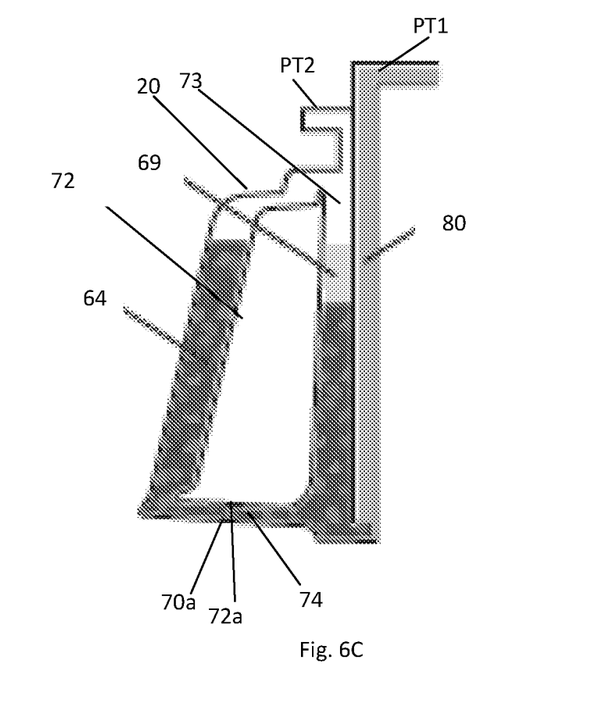
Figure 6D:
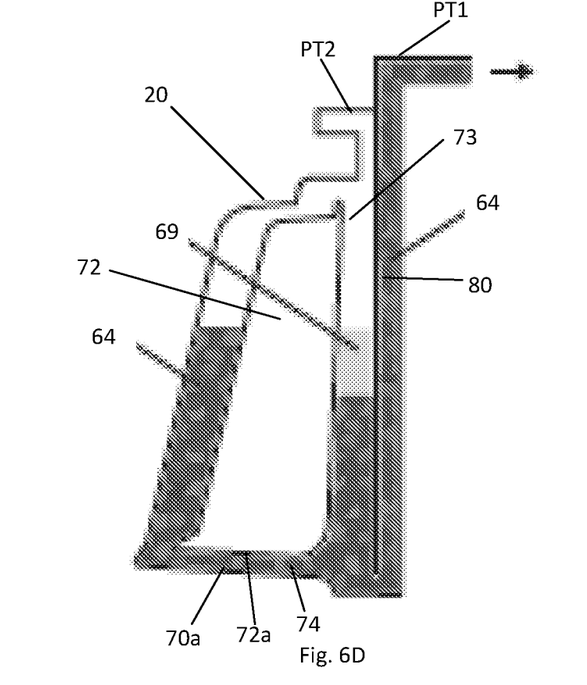

When the bowl 20 full, the method 100/controller stops the rotation of the bowl 20 (Step 115) and transfers a portion of the fluid within the bowl 20 back toward the reservoir 16 (Step 120) (FIGS. 6C and 6D) via the feed/inlet tube 80 and tube 30 (see FIGS. 1 and 3). As shown in FIGS. 6A-6I, the inlet/feed tube 80 extends from the inlet port PT1 to the bottom of the bowl 20. Therefore, the fluid transferred from the bowl 20 back toward the reservoir 16 will be drawn from the bottom of the bowl 20. As also shown in FIG. 6C, when the bowl 20 is stopped, the fat 69 will collect at the top of the fluid contained within the core 72 of the bowl 20 (e.g., within the space 73 within the core 72) and the red blood cells may re-suspend within the plasma. Therefore, the fluid that is removed during this "fluid split" is mainly red blood cells and plasma (e.g., red blood cells re-suspended within plasma) (FIG. 6D).

It should be noted that although the amount of fluid removed from the bowl 20 in step 120 can vary based on a number of factors (e.g., the size of the bowl 20, the application, the amount of fat collected within the bowl 20, etc.), a volume should be selected that prevents the fat from being removed from the bowl 20 (e.g., such that the fat remains within the bowl 20 as shown in FIG. 6D). For example, to ensure that fat is not drawn from the bowl 20 via the feed/inlet tube 80, the system may remove 20-30 mL of fluid (e.g., 25 mL) from the bowl 20 during the first fluid split. Also, depending on the length of the reservoir line 30 (and the amount of fluid removed), the volume removed during the first fluid split may not return all the way back to the reservoir 16 and, some or all of the volume may remain in the reservoir line 30.

Figure 6E:
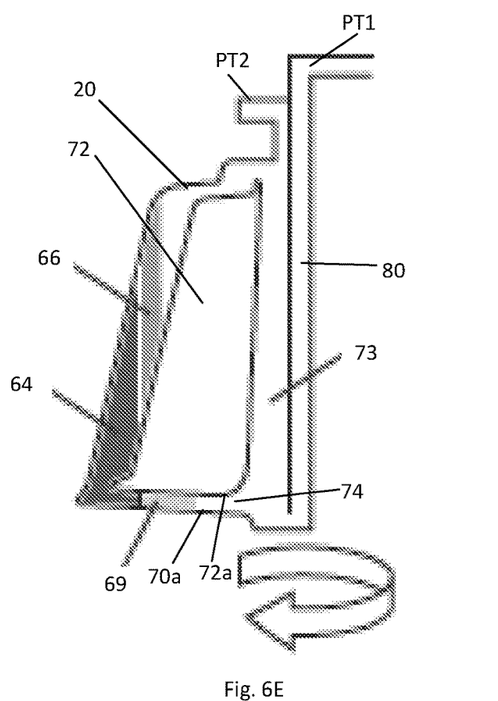
Figure 6F:
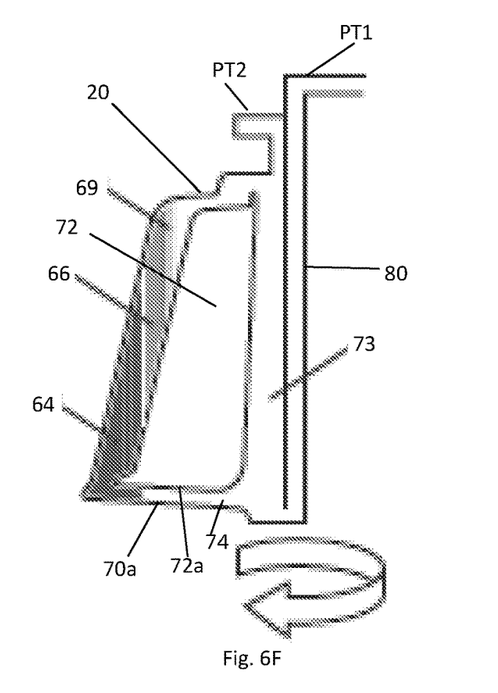

Once the fluid has been transferred to the reservoir 16/reservoir line 30, the method 100/controller may restart the centrifuge 20 and re-centrifuge the blood/fluid remaining in the bowl 20, for example, at 5650 RPM (Step 125) (FIG. 6E). By removing the fluid from the bowl 20, the method 100 creates an air pocket within the bowl 20 and temporarily reduces the red blood cell packing within the bowl 20. This air pocket and reduction in RBC packing allows the fat to pass through the red blood cell product within the bowl 20 (e.g., as the blood is re-centrifuged) (FIG. 6F). At this point, the fat 69 is located above the red blood cells 64 and the plasma 66 in the separation chamber 76 and creates a white band above the red blood cells 64 and the plasma 66.

Figure 6G:
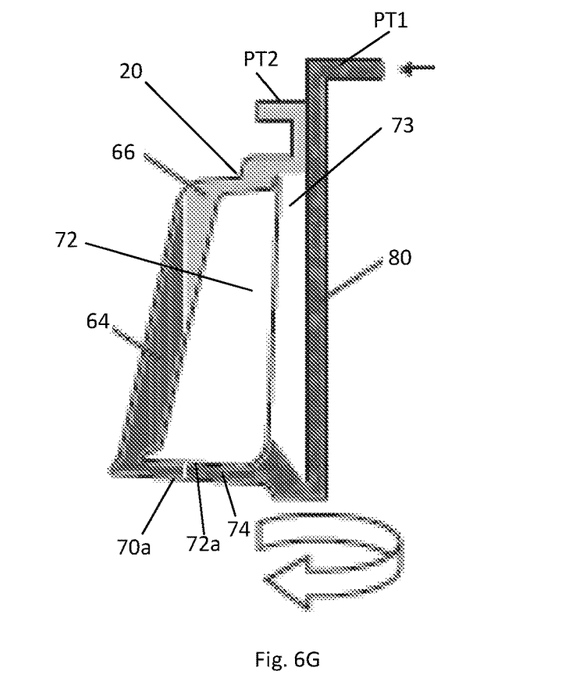

After re-centrifuging the blood within the bowl 20 for a predetermined period of time (e.g., between 40 and 60 seconds, preferably 50 seconds), the method 100 may refill the bowl 20 with fluid from the reservoir line 30 and/or reservoir 16 (Step 130; FIG. 6G). For example, the controller may energize the pump P and transfer 25 mL (e.g., the same volume removed during the fluid split discussed above) from the reservoir 16 and/or the line 30 to the bowl 20 via line 30. As shown in FIG. 6G the volume returned to the bowl 20 may include the re-suspended red blood cells that were previously removed.

Figure 6H:
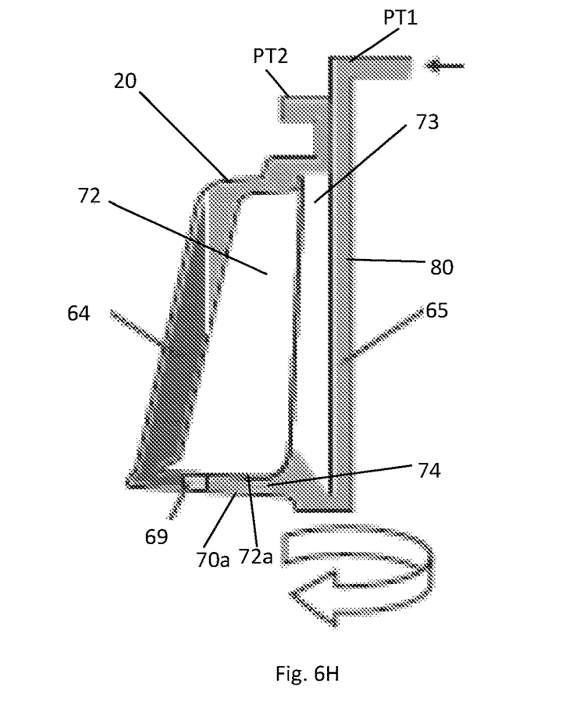

The method may then wash the blood within the bowl 12 to remove the fat (Step 135; FIG. 6H). For example, during the wash, a predetermined amount of wash solution 65 may be pumped from the wash solution bag 18 into the centrifuge bowl 20 by the pump P and via the wash line 34, valve $V_2$, line 30 and inlet port PT1 (with valves $V_1$ and $V_3$ closed and valve $V_2$ open). As the wash solution 65 (e.g., 0.9% saline solution) enters the separation chamber 76 (e.g., via passageway 74), the wash solution 65 will flow through the separated blood components and wash the fat (and other elements such as plasma, free Hgb, cellular debris, anticoagulant, etc.) from the separated blood components. In particular, as the wash solution enters the bowl 20, the wash solution displaces the fat (and other undesirable elements and, perhaps, plasma and wash solution) into the waste container 22 via the outlet port $PT_2$ and effluent line 36. As shown in FIG. 6H, during the refill and wash processes (e.g., steps 130 and 135) additional fat 69 may begin to separate from fluid within the bowl and collect behind the red blood cells 64.

The wash step may continue until the optical sensor 7 determines that the fluid exiting the bowl 20 (e.g., via the effluent line 37) is clean (e.g., 95% of fHGB, heparin, potassium, albumin, etc. have been washed out) and/or the predetermined volume of wash fluid has entered/circulated through the bowl 20. Once the wash step is complete, the controller will stop the pump P and close valve $V_2$, terminating the flow of wash solution into the centrifuge bowl 20. If no additional washing is required, the controller may stop the rotation of the centrifuge bowl 20, and reverse the pump P to pump the washed blood components remaining in the centrifuge bowl 20 into the collection bag 24 via line 30, valve $V_3$ and line 32 (with valves $V_1$ and $V_2$ closed and valve $V_3$ open). The collected blood components can then be stored for later use or reinfused into patient 12.

Figure 4:
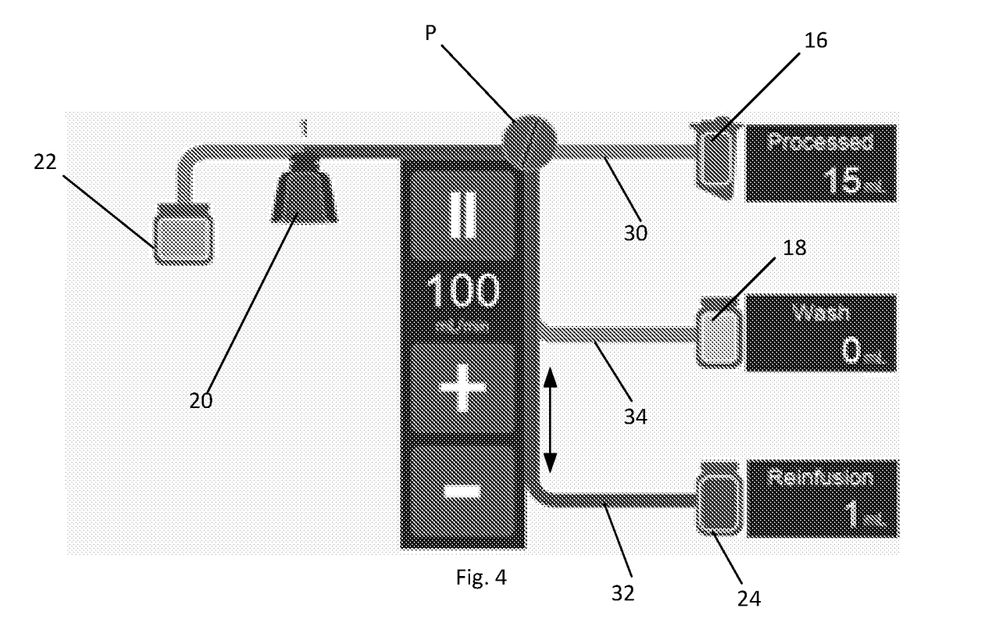
FIG. 4 schematically shows the transfer of washed blood components from the separation device to a product container of the system shown in FIG. 1, in accordance with embodiments of the present invention.
Figure 6I:
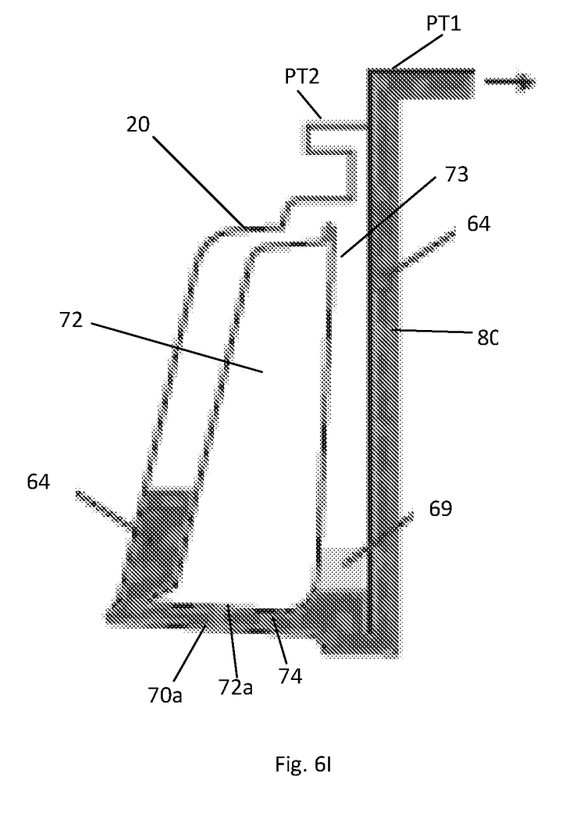

Alternatively, if the user/technician determines that there is additional fat within the bowl 20 that should be removed (e.g., by visually inspecting the bowl 20, based on the amount of fat removed during the first wash cycle, etc.), the method 100 may perform a second fat wash. For example, as noted above, during the re-fill and wash cycles (Steps 130 and 135), additional fat 69 may begin to separate from the red blood cells 64 and plasma 66 and collect behind/below the red blood cells (FIG. 6H). In such cases, the method 100/controller may once again stop the bowl (Step 140), causing the remaining fat within the bowl 20 to gather within the core 72 of the bowl 20 (e.g., in a manner similar to that discussed above and shown in FIG. 6B). The method 100/controller may then empty a portion of the fluid (e.g., the washed components) within the bowl 20 (Step 145; FIG. 4 and FIG. 6I) into the product container/collection container 24 by reversing the pump P and drawing the fluid (e.g. washed blood components) through the inlet/feed tube 80 and out the inlet PT1.

The volume of washed components that is removed during this step may vary based on the application, bowl size, whether additional washing/fat removal is required, etc. For example, in some instances, the method 100/controller may remove a larger volume than what was removed in the step 120 (e.g., the method 100/controller may remove ⅔ of the volume of fluid within the bowl). Alternatively, the method 100/controller may remove approximately the same volume as that removed during step 120 (e.g., between 20-30 mL). Also, depending on the length of the line 32 (and the amount of fluid removed), the volume removed during the second fluid split may not reach the product container 34 and, some or all of the volume may remain in the line 32. In either case and in a manner similar to that discussed above for Step 120, because the fat is collected within the core 73 (e.g., within space 73) and on top of the other components in the bowl 20, the fluid removed during Step 145 will not include fat (e.g., it will be red blood cells, plasma, etc.).

After removing the washed components from the bowl 20, the method 100/controller may, once again, restart the bowl 20 and re-centrifuge the fluid/components remaining within the bowl 20 (e.g., for 40-60 seconds, preferably for 50 seconds at 5650 RPM) (Step 150). This, in turn, causes the fat to pass through the red blood cell product (e.g., because of the air volume and reduction in packing discussed above). The method 100/controller may then re-energize the pump P and return the washed blood components that were previously transferred to the product container/collection container 24 back to the bowl 20 to re-fill the bowl 20 (Step 155).

Once the bowl 20 has been refilled, the system/method 100 may perform a second wash (Step 160) to remove the additional fat from the bowl 20. Like the first wash, during the second wash, the pump P transfers wash solution from the wash solution bag 18 into the centrifuge bowl 20 via the wash line 34, valve $V_2$, line 30 and inlet port PT1. As the wash solution (e.g., 0.9% saline solution) enters the separation chamber 76 (e.g., via passageway 74), the wash solution will flow through the separated blood components and wash the additional fat (and other remaining undesirable elements such as free Hgb, cellular debris, anticoagulant, etc.) from the separated blood components. The additional fat washed from the separated blood components is, once again, displaced into the waste container 22 by the incoming wash solution via outlet port $PT_2$ and effluent line 36.

After a predetermined volume of wash fluid has entered/circulated through the bowl 20 (e.g., 50 mL of wash solution for 70 mL bowls and 100 mL of wash solution for 125 mL and 225 mL bowls), the second wash step is complete, and the controller will stop the pump P and close valve $V_2$, terminating the flow of wash solution into centrifuge bowl 20. The system/controller will then reverse the pump P to pump the washed blood components remaining in centrifuge bowl 20 into the collection bag 24 via line 30, valve $V_3$ and line 32 (with valves $V_1$ and $V_2$ closed and valve $V_3$ open). As discussed above, the washed components can be stored for later use or re-infused into the patient 12.

It should be noted that the first fat wash step (Step 135) typically removes a large majority (e.g., 80-85%) of the fat contained within the bowl 20. Therefore, in some embodiments, the second fat wash step (Step 160) need not be a full wash step. For example, the second fat wash may be a reduced wash step and may only circulate approximately 50-100 mL of wash solution, whereas the first fat wash step may circulate approximately 500-1000 mL of wash solution through the bowl 20.

Figure 7:
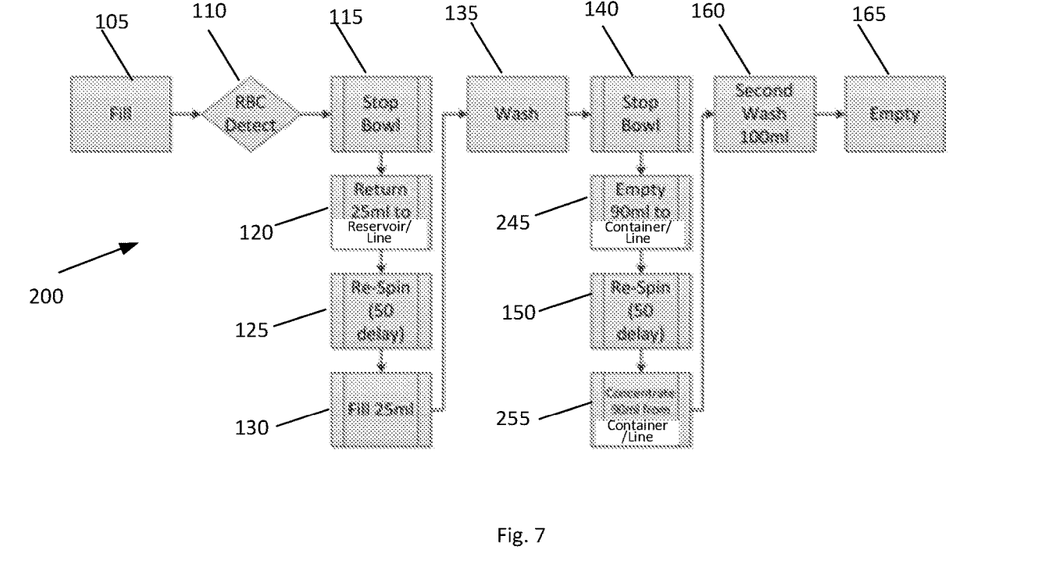
FIG. 7 is a flowchart depicting an alternative method of washing fat from shed blood, in accordance with some embodiments of the present invention.
Figure 8:
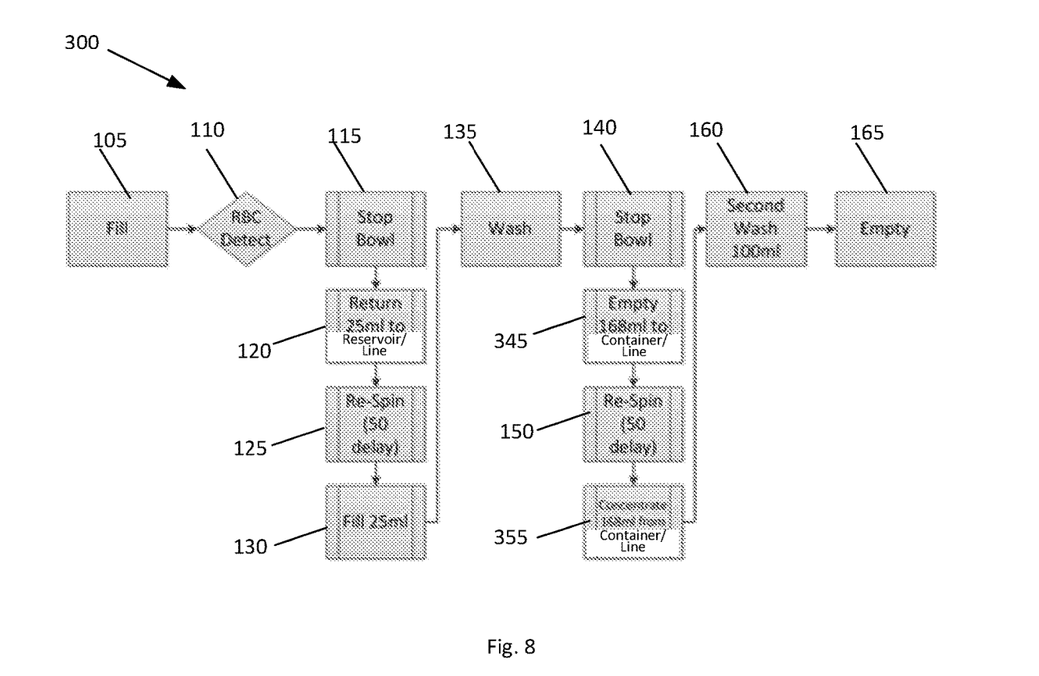
FIG. 8 is a flowchart depicting a further alternative method of washing fat from shed blood, in accordance with additional embodiments of the present invention.

Although the method 100 described above was for a 70 mL centrifuge bowl 20, the fat wash method may be used for bowls of varying sizes. For example, FIGS. 7 and 8 are flowcharts depicting methods 200/300 for washing fat from 125 mL and 225 mL bowls 20, respectively. As shown in FIGS. 7 and 8, the steps of the fat washing method are nearly identical for the various bowl sizes. However, during the second fluid split (just prior to the second wash; Step 160), the fluid emptied from the bowl 20 (Steps 245 and 345) and subsequently returned to the bowl 20 (Steps 255 and 355) from the product container/collection container 24, as well as the volume of wash solution used during the second wash may be dependent upon the bowl size. For example, for a 125 mL bowl (FIG. 7), the method 200/controller can empty and return between 80 and 100 mL of fluid (e.g., 90 mL), and the second fat wash may use 100 mL of wash solution (e.g., as compared to 50 mL for the 70 mL bowl). For a 225 mL bowl 20, the method 300/controller may empty and return between 160 and 175 mL of fluid (e.g., 168 mL), and the second fat wash may use 100 mL of wash solution.

As mentioned above, the second fluid split may be skipped in some embodiments, for example, depending upon the amount of fat collected in the reservoir 16 and/or contained within the bowl 20, or if the user/technician did not see/collect fat during the first fat wash. In a similar manner, the user/technician may skip the first fluid split (e.g., the fluid split prior to the wash step, step 135) and only perform the second fluid split (e.g., the fluid split after the wash step, step 135). To that end, the user/technician may decide to skip the fat reduction steps at various points during the salvage/wash process. For example, the user/technician may decide to skip the fat reduction steps just prior to step 120 (e.g., to skip the first fluid split), just prior to step 145/245/345 (e.g., to skip the second fluid split), and/or at step 155/255/355 to skip the second wash step (Step 160). Additionally or alternatively, the user may manually turn off the first and/or second fluid split prior to the start of the procedure (e.g., prior to connecting the reservoir 16 to the system and/or activating the pump P to fill the bowl 20). The user may manually shut off the first and/or second fluid split by entering the system settings on the blood processing device and selecting which fluid split to perform and/or which to skip. By skipping one or both of the fluid splits, the cycle time would decrease, but the amount of fat that is removed during the wash step may decrease.

It should be noted that the embodiments described above are able to remove/wash the fat from the salvaged/collected blood without damaging the individual blood components. For example, as is known in the art, centrifuging whole blood and/or red blood cells at very high speeds can damage the red blood cells contained within the centrifuge device (e.g., the bowl 20). Various embodiments of the present invention are able avoid damaging the red blood cells (and other blood components) within the bowl 20 by keeping the centrifuge speeds relatively low and in-line with typical blood processing procedures.

It is important to note that, although the above systems and methods are shown and described in relation to washing fat from salvaged blood (e.g., blood collected from a wound or surgical site), this is for illustration purposes only. Various embodiments of the present invention can be used in any number of blood processing procedures and may be used to wash fat from whole blood. For example, some embodiments may be used to wash fat from whole blood drawn and/or collected from a donor during apheresis procedures (e.g., plasmapheresis), red blood cell and/or platelet collection procedures, and/or whole blood washing procedures, etc. Additionally or alternatively, some embodiments of the present invention may be used in conjunction with a filtration device (e.g., in addition to or instead of the centrifuge bowl).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for removing fat from salvaged blood, the method comprising:
   (a) transferring salvaged blood from a reservoir to a blood component separation device, the salvaged blood filling the blood component separation device;
   (b) separating the salvaged blood into a plurality of blood components;
   (c) transferring a volume of unwashed blood components from the blood component separation device back toward the reservoir;
   (d) re-centrifuging the blood components remaining within the blood component separation device;
   (e) transferring additional salvaged blood from the reservoir to the blood component separation device, thereby refilling the blood component separation device;
   (f) introducing wash solution into the blood component separation device, the wash solution displacing a volume of fat from the blood component separation device into a waste container; and
   (g) emptying the washed blood components within the blood component separation device to a product container.

2. A method according to claim 1, further comprising:
transferring, prior to emptying the washed blood components to the product container, a volume of washed blood components from the blood component separation device to the product container;
re-centrifuging the washed blood components remaining within the blood component separation device;
returning the volume of washed blood components from the product container to the blood component separation device, thereby refilling the blood component separation device; and
introducing additional wash solution into the blood component separation device, the additional wash solution displacing a second volume of fat from the blood component separation device into a waste container.

3. A method according to claim 2, wherein the blood component separation device is a 70 mL centrifuge bowl, the volume of unwashed blood component transferred toward the reservoir being between 20 and 30 mL.

4. A method according to claim 3, wherein the volume of additional salvaged blood transferred in step (e) is equivalent to the volume of unwashed blood component transferred to the reservoir.

5. A method according to claim 3, wherein the volume of washed blood components transferred to the product container is between 20 and 30 mL.

6. A method according to claim 3, wherein introducing additional wash solution into the blood component separation device includes introducing 50 ml of wash solution.

7. A method according to claim 2, wherein the blood component separation device is a 125 mL centrifuge bowl, the volume of unwashed blood component transferred toward the reservoir being between 20 and 30 mL.

8. A method according to claim 7, wherein the volume of additional salvaged blood transferred in step (e) is equivalent to the volume of unwashed blood component transferred toward the reservoir.

9. A method according to claim 7, wherein the volume of washed blood components transferred to the product container is between 80 and 100 mL.

10. A method according to claim 7, wherein introducing additional wash solution into the blood component separation device includes introducing 100 ml of wash solution.

11. A method according to claim 2, wherein the blood component separation device is a 225 mL centrifuge bowl, the volume of unwashed blood component transferred toward the reservoir being between 20 and 30 mL.

12. A method according to claim 11, wherein the volume of additional salvaged blood transferred in step (e) is equivalent to the volume of unwashed blood component transferred toward the reservoir.

13. A method according to claim 11, wherein the volume of washed blood components transferred to the product container is between 160 and 180 mL.

14. A method according to claim 11, wherein introducing additional wash solution into the blood component separation device includes introducing 100 ml of wash solution.

15. A method according to claim 1, further comprising:
monitoring the separation of salvaged blood within the blood component separation device to detect when the blood component separation device is full; and
stopping the blood component separation device when the blood component separation device is full and prior to step (c).

16. A method according to claim 1, wherein the volume of unwashed blood components transferred to the reservoir includes red blood cells.

17. A method according to claim 1, wherein re-centrifuging in step (d) causes fat within the blood component separation device to pass through a red blood cell product within the blood component separation device and toward an outlet of the blood component separation device.

18. A method according to claim 1, further comprising stopping the blood component separation device prior to step (c).

19. A method according to claim 1, wherein at least a portion of the volume of unwashed blood components transferred back toward the reservoir remains within a reservoir line fluidly connecting the reservoir and the blood component separation device.

20. A method according to claim 19, wherein the additional salvaged blood includes the volume of unwashed blood components transferred back toward the reservoir.

21. A method for removing fat from salvaged blood, the method comprising:
(a) transferring salvaged blood from a reservoir to a blood component separation device, the salvaged blood filling the blood component separation device;
(b) separating the salvaged blood into a plurality of blood components;
(c) introducing wash solution into the blood component separation device, the wash solution displacing a volume of unwanted components from the blood component separation device into a waste container;
(d) transferring, a volume of washed blood components from the blood component separation device to a product container;
(e) re-centrifuging the washed blood components remaining within the blood component separation device;
(f) returning the volume of washed blood components from the product container to the blood component separation device, thereby refilling the blood component separation device;
(g) introducing additional wash solution into the blood component separation device, the additional wash solution displacing a volume of fat from the blood component separation device into a waste container; and
(h) emptying the washed blood components within the blood component separation device to a product container.

22. A method according to claim 21, further comprising stopping the blood component separation device prior to step (d).

23. A method according to claim 21, wherein the blood component separation device is at least one selected from the group consisting of a 70 mL centrifuge bowl, a 125 mL centrifuge bowl, and a 225 mL centrifuge bowl.

24. A method according to claim 21, wherein the volume of washed blood components transferred to the product container is between 20 and 30 mL.

25. A method according to claim 21, wherein the blood component separation device is a 70 mL centrifuge bowl and introducing additional wash solution into the blood component separation device includes introducing 50 ml of wash solution.

26. A method according to claim 21, wherein the blood component separation device is a 125 mL centrifuge bowl and introducing additional wash solution into the blood component separation device includes introducing 100 ml of wash solution.

27. A method according to claim 21, wherein the blood component separation device is a 225 mL centrifuge bowl and introducing additional wash solution into the blood component separation device includes introducing 100 ml of wash solution.

28. A method according to claim 21, wherein the volume of washed blood components transferred to the product container is between 80 and 100 mL.

29. A method according to claim 21, wherein the volume of washed blood components transferred to the product container is between 160 and 180 mL.

30. A system for washing fat from salvaged blood, the system comprising:
a reservoir configured to collect salvaged blood from a patient;
a rotatable centrifuge bowl fluidly connected to the reservoir and configured to separate the salvaged blood into a plurality of blood components;
a product container fluidly connected to the rotatable centrifuge bowl and configured to collect a washed blood component;
a waste container fluidly connected to an outlet of the rotatable centrifuge bowl and configured to collect a waste product from the centrifuge bowl;
a pump configured to control the flow of fluid through the system; and
a controller configured to control the operation of the pump and centrifuge bowl to transfer a first volume of unwashed blood components from the centrifuge bowl back toward the reservoir, re-centrifuge the blood components remaining within the centrifuge bowl, refill the centrifuge bowl with salvaged blood from the reservoir, and introduce wash solution into the centrifuge bowl, the wash solution displacing a volume of fat from the centrifuge bowl into the waste container.

31. A system according to claim 30, wherein the controller is further configured to empty the washed blood components within the centrifuge bowl to the product container.

32. A system according to claim 30, wherein the controller is configured to control the pump and centrifuge bowl to transfer a volume of washed blood components from the blood component separation device to the product container, re-centrifuge the washed blood components remaining within the blood component separation device, and return the volume of washed blood components from the product container to the blood component separation device, thereby refilling the blood component separation device.

33. A system according to claim 32, wherein the controller is further configured to control the pump to introduce additional wash solution into the centrifuge bowl, the additional wash solution displacing a second volume of fat from the centrifuge bowl into the waste container.

34. A system according to claim 30, wherein the centrifuge bowl is at least one selected from the group consisting of a 70 mL centrifuge bowl, a 125 mL centrifuge bowl, and a 225 mL centrifuge bowl.

35. A system according to claim 30 further comprising an optical sensor configured to monitor the separation of salvaged blood within the centrifuge bowl and detect when the centrifuge bowl is full.

36. A system according to claim 30, wherein the first volume of unwashed blood components includes red blood cells.

37. A method for removing fat from salvaged blood, the method comprising:
   (a) transferring salvaged blood from a reservoir to a blood component separation device, the salvaged blood filling the blood component separation device;
   (b) separating the salvaged blood into a plurality of blood components;
   (c) transferring a volume of unwashed blood components from the blood component separation device back to a reservoir line fluidly connecting the reservoir and the blood component separation device;
   (d) re-centrifuging the blood components remaining within the blood component separation device;
   (e) returning the volume of unwashed blood components from the reservoir line to the blood component separation device, thereby refilling the blood component separation device;
   (f) introducing wash solution into the blood component separation device, the wash solution displacing a volume of fat from the blood component separation device into a waste container; and
   (g) emptying the washed blood components within the blood component separation device to a product container.

38. A method according to claim 37, further comprising:
   transferring, prior to emptying the washed blood components to the product container, a volume of washed blood components from the blood component separation device to the product container;
   re-centrifuging the washed blood components remaining within the blood component separation device;
   returning the volume of washed blood components from the product container to the blood component separation device, thereby refilling the blood component separation device; and
   introducing additional wash solution into the blood component separation device, the additional wash solution displacing a second volume of fat from the blood component separation device into a waste container.

39. A method according to claim 38, wherein the blood component separation device is a 70 mL centrifuge bowl, the volume of unwashed blood component transferred to the reservoir line being between 20 and 30 mL.

40. A method according to claim 39, wherein the volume of washed blood components transferred to the product container is between 20 and 30 mL.

41. A method according to claim 39, wherein introducing additional wash solution into the blood component separation device includes introducing 50 ml of wash solution.

42. A method according to claim 38, wherein the blood component separation device is a 125 mL centrifuge bowl, the volume of unwashed blood component transferred to the reservoir line being between 20 and 30 mL.

43. A method according to claim 42, wherein the volume of washed blood components transferred to the product container is between 80 and 100 mL.

44. A method according to claim 42, wherein introducing additional wash solution into the blood component separation device includes introducing 100 ml of wash solution.

45. A method according to claim 38, wherein the blood component separation device is a 225 mL centrifuge bowl, the volume of unwashed blood component transferred to the reservoir line being between 20 and 30 mL.

46. A method according to claim 45, wherein the volume of washed blood components transferred to the product container is between 160 and 180 mL.

47. A method according to claim 45, wherein introducing additional wash solution into the blood component separation device includes introducing 100 ml of wash solution.

48. A method according to claim 37, further comprising:
   monitoring the separation of salvaged blood within the blood component separation device to detect when the blood component separation device is full; and
   stopping the blood component separation device when the blood component separation device is full and prior to step (c).

49. A method according to claim 37, wherein the volume of unwashed blood components transferred to the reservoir line includes red blood cells.

50. A method according to claim 37, wherein the volume of unwashed blood components transferred to the reservoir line includes red blood cells suspended in plasma.

51. A method according to claim 37, wherein re-centrifuging in step (d) causes fat within the blood component separation device to pass through a red blood cell product within the blood component separation device and toward an outlet of the blood component separation device.

52. A method according to claim 37, further comprising stopping the blood component separation device prior to step (c).

* * * * *